United States Patent [19]

Roos

[11] 4,147,722

[45] Apr. 3, 1979

[54] MONO-, BIS- AND TRIS-SULPHENYL CHLORIDES

[75] Inventor: Ernst Roos, Odenthal-Osenau, Fed. Rep. of Germany

[73] Assignee: Bayer Aktiengesellschaft, Fed. Rep. of Germany

[21] Appl. No.: 577,074

[22] Filed: May 13, 1975

[30] Foreign Application Priority Data

May 18, 1974 [DE] Fed. Rep. of Germany ....... 2424248

[51] Int. Cl.² .......................................... C07C 145/00
[52] U.S. Cl. ................................................. 260/543 H
[58] Field of Search .................................... 260/543 H

[56] References Cited

U.S. PATENT DOCUMENTS

| | | |
|---|---|---|
| 2,774,707 | 12/1956 | Birum ............................. 260/543 H |
| 2,944,080 | 7/1960 | Johnston ........................ 260/543 H |
| 3,185,621 | 5/1965 | Margot ........................... 260/543 H |
| 3,474,139 | 10/1969 | Leib ................................ 260/543 H |
| 3,766,236 | 10/1973 | Thaler et al. ................... 260/543 H |

*Primary Examiner*—Norman Morgenstern
*Attorney, Agent, or Firm*—Connolly and Hutz

[57] ABSTRACT

Mono-, di- and tri-(chloro sulphenyl methyl)-perchlorobenzenes are produced by chlorinating mercapto methyl perchlorobenzenes of the formula

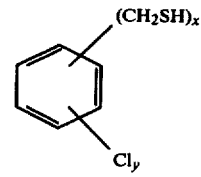

x being 1 to 3 and y 6−x.

The new compounds can be used as starting materials for producing compounds of the sulphene amide type or may be added to rubber for crosslinking purposes.

6 Claims, No Drawings

MONO-, BIS- AND TRIS-SULPHENYL CHLORIDES

Sulphenyl chlorides are commercially produced by the action of chlorine or sulphuryl chloride on disulphides or mercaptans (cf. The Chemistry of the Sulfenic Acids by E. Kuhle, Georg Thieme Publishers Stuttgart, 1973, pages 5 to 16).

Unfortunately, processes of this kind cannot be used for the production of benzyl sulphenyl chlorides from benzyl disulphides or benzyl mercaptans because, even at low temperatures, it is only the corresponding benzyl chlorides and sulphur chlorides which are formed (cf. loc. cit., page 6):

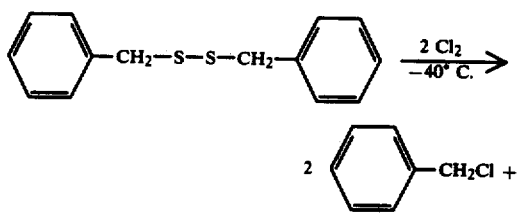

Aryl benzene sulphides also split between the sulphur atom and the benzyl radical to form, in addition to the aryl sulphenyl chloride, the benzyl chloride and not the benzyl sulphene chloride (cf. loc. cit., page 16):

These reactions show that, in general, compounds with the group —CH$_2$SCl on the aromatic nucleus cannot be produced by the types of process normally worked on a commercial scale.

The present invention provides a process for the production of mono-, di- and tri-(chlorosulphenyl methyl)-perchlorobenzenes corresponding to the formula (I)

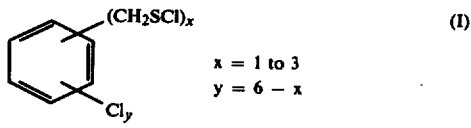

which is characterised by the fact that mono-, di- or tri-(mercaptomethyl)-perchlorobenzenes corresponding to the formula (II)

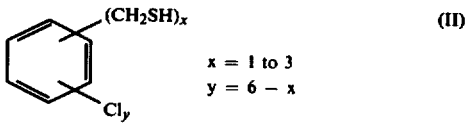

or the corresponding (poly)disulphides are chlorinated, optionally in an inert solvent.

The invention also provides mono-, di- and tri-(chlorosulphenyl) methyl)-perchlorobenzenes corresponding to the formula (I)

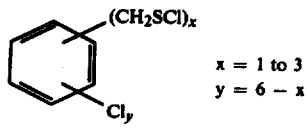

Starting materials suitable for use in the process according to the invention are, in particular, mono-, di- and tris-mercaptans completely chlorinated in the nucleus and corresponding to formulae IIa, IIb and IIc, below:

Cl Cl Cl         (CH$_2$SH)$_2$         Cl   CH$_2$SH
    CH$_2$SH              HS—CH$_2$—   —Cl
Cl Cl                (Cl)$_4$         Cl   CH$_2$SH

IIa              IIb              IIc

These mercaptans and methods for their production are known. For example, benzyl, xylylene and mesitylene chlorides completely chlorinated in the nucleus may be reacted with sodium hydrogen sulphide or NaSH, or alternatively isothiouranium salts containing the group $$-CH_2-S-C\underset{NH_2}{\overset{NH \cdot HCl}{\diagup}}$$

or Bunte salts containing the group

—CH$_2$—S—SO$_3$Na may be split.

The isomeric tetrachloro-(o-,m-,p)-xylylene-bis-mercaptans are obtained in the form of a mixture, for example by the following reaction: commercial-grade xylylene isomer mixture is 1. completely chlorinated in the nucleus,
2. chlorinated in the side chains, in each case up to the —CH$_2$Cl—stage,
3. reacted with sodium thiosulphate to form the double Bunte salt: —CH$_2$S.SO$_3$Na and split with acid to form the bis-mercaptan isomer mixture.

The (poly)disulphides which may also be used as starting compounds can be obtained for example by oxidising the corresponding mercaptans with hydrogen peroxide, sodium hypochlorite or chlorine by conventional methods.

The process according to the invention may generally be carried out by reacting a mercaptan completely chlorinated in the nucleus of formula II, IIa, IIb or IIc, or a corresponding (poly)disulphide, with a chlorinating agent in an inert organic solvent at temperatures in the range from −20° to +120° C. and preferably at temperatures in the range from +20° to +100° C. Chlorine and sulphuryl chloride represent particularly suitable chlorinating agents.

Suitable inert solvents are, for example, chlorinated aliphatic hydrocarbons such as methylene chloride, chloroform, carbon tetrachloride, dichloroethane, trichloroethane, tetrachloroethane, dichlorethylene, trichlorethylene, tetrachlorethylene; aromatic hydrocarbons such as benzene, toluene, xylene; chlorinated aromatic hydrocarbons such as chlorbenzene, dichlorbenzene and trichlorbenzene.

The chlorinating agent is preferably used in a stoichiometric quantity, although it can be of advantage in some cases to use a small excess or alternatively a deficit.

The following new sulphenyl chlorides in particular may be obtained by the process according to the invention: chlorosulphenyl methyl pentachlorobenzene, p-bis-(chlorosulphenyl methyl)-tetrachlorobenzene, m-bis-(chlorosulphenyl methyl)-tetrachlorobenzene, an isomeric mixture of o-, m-, p-bis-(chlorosulphenyl methyl)-tetrachlorobenzene, 1,3,5-tris-(chlorosulphenyl methyl)-2,4,6-trichlorobenzene.

The new sulphenyl chlorides (I) are, for example, starting product for producing rubber vulcanizing agents of the sulphenyl amide type.

The bis- and tris-sulphenyl chlorides may also be used for crosslinking natural and synthetic rubbers at temperatures as low as normal temperature.

The invention is illustrated by the following Examples:

1. Pentachlorobenzyl sulphenyl chloride:

89 g (0.3 mol) of pentachlorobenzyl mercaptan were introduced into 400 ml of chlorobenzene, followed by the addition at 20° C. to 40° C. of 41 g (0.3 mol) of sulphuryl chloride, $SO_2$ and HCl being given off. The mixture was stirred for 2 hours at 80° C. until there was no further evolution of gas. The solution formed was distilled in vacuo at 80° C. and the residue recrystallised from light petrol.

Yield: 67 g (68% of the theoretical yield) of yellowish crystals, m.p. 95°–97° C.

$C_7H_2Cl_6S$ (MW 331) MW mass spectroscop found: 328 (chlorine isotope 35).

Calculated: C 25.38; H 0.60; Cl 64.35; S 9.67 Found: 26.0; 0.8; 63.9; 9.1.

The same product was obtained when chlorine was used instead of $SO_2Cl_2$ or when methylene chloride or chloroform was used instead of chlorobenzene.

The same product was obtained in a yield of 82% of the theoretical yield when pentachlorobenzyl disulphide was used instead of pentachlorobenzyl mercaptan.

2. Tetrachloro-p-xylylene-bis-sulphenyl chloride:

Chlorine was introduced at 20° to 40° C. into a mixture of 61.6 g (0.2 mol) of tetrachloro-p-xylylene-bis-mercaptan and 300 ml of chlorobenzene until an increase in weight of 16 g had occurred, accompanied by the evolution of HCl. The mixture was stirred for 1 hour at 25° to 40° C. and then heated to 95° C., resulting in the formation of a clear yellow solution. This solution was cooled to 0°–10° C., as a result of which yellow crystals precipitated. They were filtered off under suction, washed with methylene chloride and then dried.

Yield: 67 g (89% of the theoretical yield) of yellowish crystals, m.p. 169°–170° C.

$C_8H_4Cl_6S_2$ (MW 377) MW mass spectroscop found: 374 (chlorine isotope 35).

Calculated: C 25.46; H, 1.06; Cl 56.50; S 16.98; Found: 26.1; 1.1; 56.1; 16.6.

The same product was obtained when $SO_2Cl_2$ was used instead of chlorine and when methylene chloride, chloroform or carbon tetrachloride was used instead of chlorobenzene.

3. Tetrachloro-m-xylylene-bis-sulphenyl chloride:

Chlorine was introduced at 20° to 40° C. into a mixture of 61.6 g (0.2 mol) of tetrachloro-m-xylylene-bis-mercaptan and 250 ml of chlorobenzene until an increase in weight of 14 g had occurred. The solution formed was distilled in vacuo at 80° C., leaving behind a viscous brown oil. Yield: 70 g (93% of the theoretical yield) of a viscous reddish-brown oil which changed in moist air, evolving HCl. $C_8H_4Cl_6S_2$ (MW 377)

Calculated: C 25.46; H, 1.06; Cl 56.50; S 16.98; Found: 24.8; 1.5; 57.5; 16.2.

The same product was obtained when $SO_2Cl_2$ was used instead of chlorine and when methylene chloride was used instead of chlorobenzene.

4. Tetrachloro-(o,m,p)-xylylene-bis-sulphenyl chloride:

59 g (0.44 mol) of sulphuryl chloride were added dropwise at 20° to 30° C. to a mixture of 61.6 g (0.2 mol) of tetrachloro-(o,m,p)-xylylene-bis-mercaptan in 300 ml of methylene chloride. The reaction mixture was boiled under reflux until the evolution of gas had ceased. Removal of the methylene chloride by distillation in vacuo left behind a viscous partly crystallised paste. Yield: 67 g (89% of the theoretical yield).

A product with the same properties was obtained when chlorine was used instead of $SO_2Cl_2$ and when chlorobenzene was used instead of methylene chloride.

Recrystallisation of the isomeric mixture from chlorobenzene gave yellow crystals melting at 159°–161° C. which, according to analysis by spectroscopy (IR-spectrums), was identical with the product produced in accordance with Example 2.

Concentration of the chlorobenzene mother liquor by evaporation in vacuo gave a brown viscous oil which was very similar to the product obtained in accordance with Example 3.

For numerous applications, however, there should be no need to separate the mixture into the individual isomers.

5. Trichloromesitylene-tris-sulphenyl chloride:

Chlorine was introduced at 20° C. to 30° C. into a mixture of 32 g (0.1 mol) of trichloromesitylene-tris-mercaptan in 300 ml of chlorobenzene until an increase in weight of 10.4 g had occurred. A clear, reddish-brown solution containing the trichloromesitylene-tris-sulphenyl chloride with the summation formula $C_9H_6Cl_6S_3$ (molecular weight 423) was formed with evolution of HCl. Since this compound decomposes in moist air with evolution of HCl following removal of the solvent, reactions are best carried out in or with the tris-sulphene chloride solution obtained.

Instead of chlorobenzene solutions, it is also possible to prepare solutions in methylene chloride, chloroform, carbon tetrachloride and tetrachlorethylene.

6. Application Examples

The crosslinking effect of the new bis- and tris-sulphenyl chlorides is illustrated in the following:

a. a 2% solution of natural rubber (NR) in toluene was stirred at 20° C. with a saturated toluene solution of tetrachloro-p-xylylene-bis-sulphenyl chloride (Example 2). After brief stirring, the natural rubber solution solidified into a gel with crosslinking.

The same crosslinking occurred when 2% to 5% solutions of nitrile-butadiene rubber (NBR), styrene-butadiene rubber (SBR), polyisoprene rubber (IR), polybutadiene rubber (BR), polychloroprene rubber (CR), ethylene-propylene-diene rubber (EPDM), butyl rubber (IIR) and other rubbers containing double bonds, were used.

b. The same crosslinking reaction was also obtained with the solutions of natural and synthetic rubbers mentioned in 6a above when the solutions of tetrachloro-m-xylylene-bis-sulphenyl chloride, tetrachloro-(o,m,p)-xylylene-bis-sulphenyl chloride and trichloromesitylene-tris-sulphenyl chloride obtained in accordance with Examples 3, 4 and 5, were used instead of tetrachloro-p-xylylene-bis-sulphenyl chloride without previous isolation of the sulphenyl chlorides.

I claim:

1. A compound of the formula

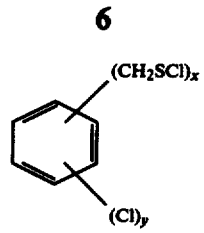

wherein x is 1 to 3 and y is 6−x.
2. Pentachlorobenzyl sulphenyl chloride.
3. Tetrachloro-p-xylylene-bis-sulphenyl chloride.
4. Tetrachloro-m-xylylene-bis-sulphenyl chloride.
5. Isomer mixture of tetrachloro-(o,m,p)-xylylene-bis sulphenyl chloride.
6. Trichloromesitylene-tris-sulphenyl chloride.

* * * * *